(12) United States Patent
Justin

(10) Patent No.: US 11,892,393 B2
(45) Date of Patent: *Feb. 6, 2024

(54) DETECTION SYSTEM AND METHOD FOR DETERMINING CONTAMINANT CONCENTRATION IN FEED WATER STREAM

(71) Applicant: A. O. SMITH CORPORATION, Milwaukee, WI (US)

(72) Inventor: Gusphyl Antonio Justin, Milwaukee, WI (US)

(73) Assignee: A.O. Smith Corporation, Milwaukee, WI (US)

( * ) Notice: Subject to any disclaimer, the term of this patent is extended or adjusted under 35 U.S.C. 154(b) by 744 days.

This patent is subject to a terminal disclaimer.

(21) Appl. No.: 17/080,303

(22) Filed: Oct. 26, 2020

(65) Prior Publication Data
US 2021/0055204 A1    Feb. 25, 2021

Related U.S. Application Data

(63) Continuation of application No. 15/864,961, filed on Jan. 8, 2018, now Pat. No. 10,837,895.

(51) Int. Cl.
*G01N 21/00* (2006.01)
*C02F 1/469* (2023.01)
(Continued)

(52) U.S. Cl.
CPC .............. *G01N 21/00* (2013.01); *B63J 4/006* (2013.01); *C02F 1/001* (2013.01); *C02F 1/008* (2013.01);
(Continued)

(58) Field of Classification Search
CPC .... G01N 21/00; G01N 27/00; G01N 27/4167; G01N 33/188; G01N 27/26;
(Continued)

(56) References Cited

U.S. PATENT DOCUMENTS 3,838,774 A    10/1974 Dolan et al.
6,451,210 B1    9/2002 Sivavec et al.
(Continued)

FOREIGN PATENT DOCUMENTS

CN    104792833 A    7/2015
EP    2363705 A1    9/2011
(Continued)

OTHER PUBLICATIONS

American Water College, "Problem Solved: BOD Removal Efficiency Problem—Wastewater Math," <https://www.youtube.com/watch?v=S0v2ycyjvWA> Mar. 2012.
(Continued)

*Primary Examiner* — Dennis White
(74) *Attorney, Agent, or Firm* — Michael Best & Friedrich LLP

(57) ABSTRACT

A system and method for treating water containing at least one contaminant. The system and method include a water treatment module such as a reverse osmosis unit. An electrochemical contaminant detection system is positioned in the waste water stream of the water treatment module. The contaminant detection system includes a contaminant sensor and a water quality sensor module. The contaminant sensor measures the concentration of the contaminant in the waste water stream and the water quality sensor module measures one or more water quality parameters of the waste water stream. A processor uses an algorithm to determine the concentration of the contaminant in the feed water based on the measurements of the contaminant sensor and water quality sensor module.

20 Claims, 1 Drawing Sheet

(51) Int. Cl.
*C02F 1/46* (2023.01)
*G01N 33/18* (2006.01)
*B63J 4/00* (2006.01)
*G01N 27/416* (2006.01)
*C02F 1/00* (2023.01)
*G01N 27/00* (2006.01)
*C02F 101/20* (2006.01)
*G01N 27/26* (2006.01)

(52) U.S. Cl.
CPC .......... *C02F 1/4602* (2013.01); *C02F 1/4698* (2013.01); *G01N 27/00* (2013.01); *G01N 27/4167* (2013.01); *G01N 33/188* (2013.01); *C02F 2101/20* (2013.01); *C02F 2209/003* (2013.01); *C02F 2209/06* (2013.01); *G01N 27/26* (2013.01)

(58) Field of Classification Search
CPC ...... G01N 33/1813; B63J 4/006; C02F 1/001; C02F 1/008; C02F 1/4602; C02F 1/4698; C02F 2101/20; C02F 2209/003; C02F 2209/06; C02F 2103/02; C02F 2209/008; C02F 2209/11; B01D 2311/18; B01D 2311/243; B01D 61/16; B01D 61/12; B01D 61/025; B01D 61/04; B01D 61/22
See application file for complete search history.

(56) References Cited

U.S. PATENT DOCUMENTS

| | | | |
|---|---|---|---|
| 7,563,351 | B2 | 7/2009 | Wilkins et al. |
| 7,604,725 | B2 | 10/2009 | Ganzi et al. |
| 7,767,093 | B2 | 8/2010 | Frank |
| 8,377,314 | B2 | 2/2013 | Frank |
| 8,535,499 | B2 | 9/2013 | Blauw et al. |
| 8,585,882 | B2 | 11/2013 | Freydina et al. |
| 8,658,043 | B2 | 2/2014 | Wilkins et al. |
| 8,894,834 | B2 | 11/2014 | Freydina et al. |
| 9,574,277 | B2 | 2/2017 | Jha et al. |
| 2002/0110924 | A1* | 8/2002 | Carr ........................ C02F 1/441 422/400 |
| 2006/0144765 | A1 | 7/2006 | Skwiot |
| 2007/0295650 | A1 | 12/2007 | Yoneda et al. |
| 2008/0185293 | A1 | 8/2008 | Klose et al. |
| 2009/0057210 | A1 | 3/2009 | Barrett et al. |
| 2011/0192720 | A1 | 8/2011 | Blauw et al. |
| 2012/0247978 | A1 | 10/2012 | Zevenbergen et al. |
| 2014/0001211 | A1 | 1/2014 | Thomas et al. |
| 2015/0352498 | A1 | 12/2015 | Raman |
| 2016/0207811 | A1 | 7/2016 | Kamito et al. |
| 2017/0166468 | A1 | 6/2017 | Gorrell et al. |
| 2017/0363563 | A1 | 12/2017 | Alvarez et al. |
| 2019/0277744 | A1 | 9/2019 | Giglia |

FOREIGN PATENT DOCUMENTS

| | | |
|---|---|---|
| EP | 2682745 A1 | 1/2014 |
| EP | 3149461 A1 | 4/2017 |
| JP | 2002205053 A | 7/2002 |
| WO | 2015184234 A1 | 12/2015 |
| WO | 2016090176 A1 | 6/2016 |
| WO | 2017058806 A1 | 4/2017 |
| WO | 2019136367 A1 | 7/2019 |

OTHER PUBLICATIONS

Andalyze, "Real-Time Water Testing," <www.andalyze.com> webpage available at least as early as Nov. 20, 2009.
Aqua Metrology Systems, "Predict Future THM Levels in the Present," <www.aquametrologysystems.com> webpage available at least as early as Dec. 4, 2010.
Gao et al., "Fully integrated wearable sensor arrays for multiplexed in situ perspiration analysis," Nature, 529: 509-526, 2016.
Gao et al., "Wearable Microsensor Array for Multiplexed Heavy Metal Monitoring of Body Fluids," ACS Sens., vol. 1: 866-874, 2016.
Guo et al., "Detection of Trace Zinc by an Electrochemical Microsensor based on Carbon Nanotube Threads," Electroanalysis, vol. 25 (7): 1599-1604, 2013.
Industrial Test Systems, Inc., "SenSafe," <www.sensafe.com> webpage available at least as early as Oct. 8, 1999.
International Preliminary Report on Patentability for Application No. PCT/US2019/012514 dated Jul. 23, 2020 (6 pages).
International Search Report and Written Opinion for Application No. PCT/US2019/012514 dated Mar. 7, 2019 (17 pages).
Lin et al., "A drinking water sensor for lead and other heavy metals," Analytical Chemistry, vol. 89 (17): 8748-8756.
Minnesota Pollution Control Agency Training and Certification Unit, "Wastewater Treatment Facility Operator's Math," <https://www.pca.state.mn.us/sites/default/files/wq-wwtp8-02.pdf> Sep. 2008.
ModernWater, "MicroTrace Brochure," <https://www.modernwater.com/pdf/MW_Trace_Metals_Brochure.pdf> Aug. 2017 ed.
NanoTube, "A real time water sensor," <https://www.youtube.com/watch?v=aE2gLDEv_BI> webpage available at least as early as Apr. 28, 2015.
Nyein et al., "A Wearable Electrochemical Platform for Noninvasive Simultaneous Monitoring of Ca2+ and pH," ACS Nano, vol. 10 (7): 7216-7224, 2016.
Zhao et al., "Electrochemical studies of three dimensional graphene foam as an electrode material," Electroanalysis, vol. 29 (6): 1-8, 2017.
Zhao et al., "Simultaneous Detection of Heavy Metals by Anodic Stripping Voltammetry Using Carbon Nanotube Thread," Electroanalysis, vol. 26 (3): 488-496, 2014.
European Extended Search Report and Written Opinion for Application No. 19736096.9 dated Jul. 19, 2021.

* cited by examiner

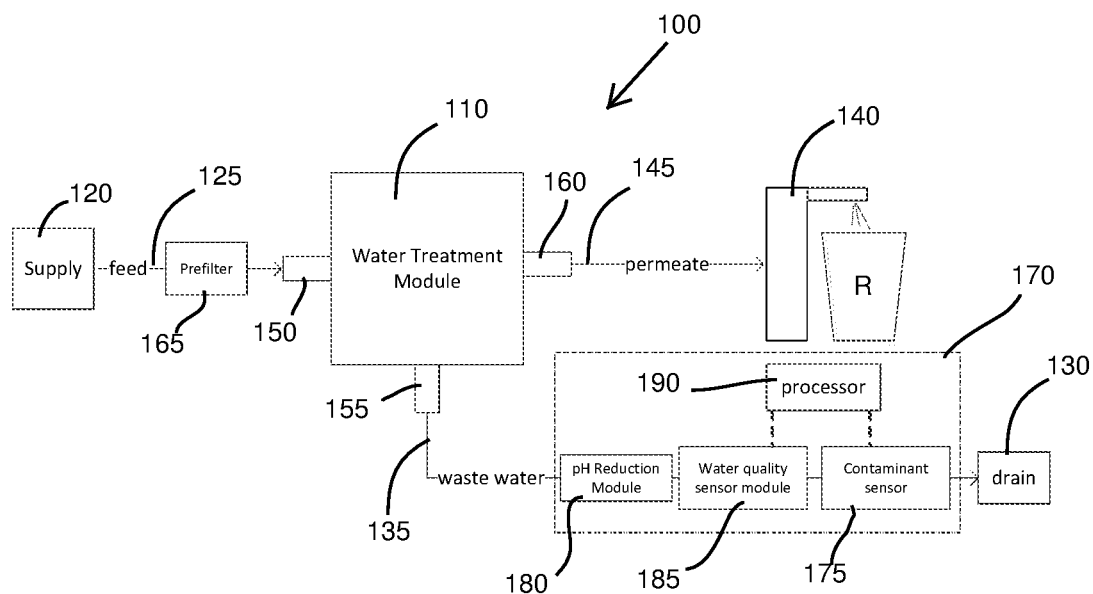

DETECTION SYSTEM AND METHOD FOR DETERMINING CONTAMINANT CONCENTRATION IN FEED WATER STREAM

CROSS-REFERENCE TO RELATED APPLICATIONS

This application is a continuation of co-pending U.S. patent application Ser. No. 15/864,961 filed on Jan. 8, 2018, the entire contents of which are incorporated herein by reference.

TECHNICAL FIELD

The present invention pertains to electrochemical sensor devices and methods for monitoring contaminants, such as heavy metals. More particularly, the present invention pertains to contaminant detection in water purification systems.

BACKGROUND

Current laboratory methods for the detection of trace concentration levels of heavy metals include such techniques as Atomic Absorption Spectroscopy (AAS) and Inductively Coupled Plasma (ICP). These involve expensive instruments on the order of tens to hundreds of thousands of U.S. dollars (USD) and require trained specialists. However, they can detect trace level concentrations of heavy metals down to the parts per trillion (ppt) and in some instances, parts per quadrillion (ppq) levels.

In terms of portable technologies, the majority of commercially available electronic heavy metal sensors are handheld systems that require some sample preparation, including the addition of a buffer solution that modifies the pH, ionic environment, and conductivity of the sample, in order to create optimal and consistent conditions for detection. For lead (Pb), these portable instruments typically have limited detection limits, for example, down to 2 parts per billion (ppb), and they rely on consumables, including chemical reagents and disposable sensor cartridges, which involves some sample preparation, such as the addition of a buffer solution.

For continuous monitoring of trace heavy metals, commercially available systems are large, bulky, expensive, and have complicated instruments that employ fluidics and pumping mechanisms and require multiple reagents, including buffers and cleaning solutions. These systems can typically measure between 1 and 4 heavy metals and have detection limits in the low ppb range (for example, 1 ppb and less).

SUMMARY OF THE INVENTION

The invention provides a system for treating water containing at least one contaminant, the system comprising: a water treatment module operable to receive a feed water stream having an original concentration of the contaminant and divide the feed water stream into a waste water stream having a concentration of the contaminant higher than the original concentration and a permeate water stream having a concentration of the contaminant lower than the original concentration; and an electrochemical contaminant detection system comprising a contaminant sensor and at least one water quality sensor; wherein the contaminant sensor measures the concentration of the contaminant in the waste water stream and the at least one water quality sensor measures at least one water quality parameter of the waste water stream; and wherein the device is configured to deduce the original concentration based on the concentration measured by the contaminant sensor and the at least one water quality parameter measured by the at least one water quality sensor.

In one aspect of the invention, the water treatment module comprises at least one of an electrical, electrochemical, physical, and non-electrochemical mechanism to separate the feed water stream into the waste water stream and permeate stream. In one aspect of the invention, the contaminant sensor is configured to measure the concentration of one or more contaminants selected from the group consisting of: dissolved solids, heavy metals, organic compounds, volatile organic compounds, biological contaminants, and scale-forming contaminants. In one aspect of the invention, the contaminant sensor comprises at least one of an electrical sensor, an electrochemical sensor, an optical sensor, and a fluorescent based sensor. In one aspect of the invention, the water quality sensor comprises at least one of a pH sensor, a conductivity sensor, a temperature sensor, an ionic strength sensor, a particle size sensor, and a fluid turbidity sensor. In one aspect of the invention, the system further comprises a processor receiving input from the water quality sensor and the contaminant sensor and calculating a contaminant concentration in the waste water stream. In one aspect of the invention, the system further comprises a prefilter upstream of the water treatment module for pretreatment of the feed water stream, the prefilter comprising at least one of a large contaminant filter, an organic material filter, a heavy metal filter, and a scale mitigation filter. In one aspect of the invention, the contaminant detection system includes an electrochemical pH reduction module for lowering the pH of the waste water stream prior to the waste water stream reaching the contaminant sensor or water quality sensor. In one aspect of the invention, the contaminant detection system comprises a handheld device.

The invention also provides a method for treating water, comprising: (a) providing a feed water stream to a water treatment module, the feed water stream having an original concentration of a contaminant; (b) dividing the feed water stream with the water treatment module into a waste water stream having a concentration of the contaminant higher than the original concentration and a permeate water stream having a concentration of the contaminant lower than the original concentration; (c) electrochemically measuring the concentration of the contaminant in the waste water stream; (d) electrochemically measuring at least one water quality parameter of the waste water stream; and (e) determining the original concentration based on the measured water quality parameter and measured concentration of the contaminant in the waste water stream.

In one aspect of the invention, step (b) includes dividing the feed water stream in a water treatment module employing at least one of an electrical, electrochemical, physical, and non-electrochemical mechanism. In one aspect of the invention, step (c) includes measuring the concentration of one or more contaminants selected from the group consisting of: dissolved solids, heavy metals, organic compounds, volatile organic compounds, biological contaminants, and scale-forming contaminants. In one aspect of the invention, step (c) includes electrochemically measuring with at least one of an electrical sensor, an electrochemical sensor, an optical sensor, and a fluorescent based sensor. In one aspect of the invention, step (d) includes electrochemically measuring with a water quality sensor comprising at least one of a pH sensor, a conductivity sensor, a temperature sensor, an ionic strength sensor, a particle size sensor, and a fluid turbidity sensor. In one aspect of the invention, the method further comprises, prior to step (a), prefiltering at least one of at least one of organic material, heavy metals, and scale from the feed water stream. In one aspect of the invention, the method further comprises electrochemically reducing pH of the waste water stream prior to steps (c) and (d). In one aspect of the invention, at least step (d) is executed with a handheld device.

BRIEF DESCRIPTION OF THE DRAWINGS

The accompanying drawing illustrates an exemplary system embodying the present invention.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)", "include(s)", "having", "has", "can", "contain(s)", and variants thereof, as used herein, are intended to be open-ended transitional phrases, terms, or words that do not preclude the possibility of additional acts or structures. The singular forms "a", "and", and "the" include plural references unless the context clearly dictates otherwise. The present disclosure also contemplates other embodiments "comprising", "consisting of", and "consisting essentially of", the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrase "at least one of A, B, . . . and N" or "at least one of A, B, . . . N, or combinations thereof" are defined in the broadest sense to mean one or more elements selected from the group comprising A, B, . . . and N, that is to say, any combination of one or more elements A, B, . . . or N including any one element alone or in combination with one or more of the other elements, which may also include, in combination, additional elements not listed.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4". The term "about" may refer to plus or minus 10% of the indicated number. For example, "about 10%" may indicate a range of 9% to 11%, and "about 1%" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The invention relates to an apparatus and method of determining the concentration of contaminants in water supplied to a water treatment module. As used herein, the term "contaminants" is intended to be a very broad term, including dissolved solids, heavy metals (e.g., lead, copper, iron, sodium, calcium, magnesium, a metal ion, oxide, or hydroxide thereof, cadmium, mercury, arsenic and their oxides), organic (carbon-based) compounds, volatile organic compounds (VOCs), biological contaminants (e.g., bacteria), contaminants such as calcium carbonate that cause scale formation, and any other elements suspended or dissolved in water. More specifically, the invention provides a potential solution for providing long term, continuous, real time detection of contaminants (such as heavy metals) without the need for chemical reagents, acids and buffers that modify the pH, ionic environment, and conductivity. The system does not require calibration despite changes to the electrode or environmental conditions.

As used herein, the term "water treatment module" is also intended to be a very broad term, including any module or system that divides feed water into waste water and permeate. "Waste water" means water having a higher concentration of contaminants than the feed water and "permeate" means water having a lower concentration of contaminants than the feed water. The term "water treatment module" includes all types of modules and systems that meet the above functional definition. Without limiting the definition, examples of water treatment modules include water filtration modules, water purification modules, and water softening modules or systems which themselves may include sub-systems and sub-modules.

The term "water treatment module" includes systems or modules that employ any mechanism for dividing the feed water into waste water and permeate. For example, and without limitation, the water treatment module may use electrical, electrochemical, physical, or non-electrochemical mechanisms, or any combination of these mechanisms, for dividing the feed water into waste water and permeate. Electrical and electrochemical mechanisms apply electrical currents across electrodes in combination with anion/cation exchange membranes or anion/cation exchange resins. The electrical currents remove ions from the water to be delivered as the permeate stream and concentrate the ions in water to be delivered as the waste water stream. Physical and non-electrochemical water treatment modules include those with filters or membranes through which the feed water passes. As such, the term "water treatment module" includes, for example, reverse osmosis (RO) membranes, multistage RO systems, ultrafiltration (UF) membranes, and nanofiltration (NF) membranes. Depending on the type of water treatment module, the permeate may be pure water, devoid of contaminants or may have a level and type of contaminants acceptable or desirable for the application.

The embodiments described herein are not limiting of the broad definition of water treatment module described above; the described embodiments are merely examples.

The drawing illustrates a system 100 including a water treatment module 110 that communicates with a water supply 120 through a feed water line 125, communicates with a drain 130 or other disposal system through a waste water line 135, and communicates with a faucet 140 or other delivery mechanism through a permeate line 145. The system 100 may be, for example, a point-of-use (POU) or point-of-entry (POE) system to treat water for dispensing into a cup or other receptacle R for the end user. The waste water stream will inherently include a higher concentration of contaminant ions than the feed water and will therefore have a higher conductivity. In this regard, the waste water stream is "preconcentrated" by the water treatment module 110 for sensors (discussed below) in the waste water line 135. Other known filters, such as a carbon filter, may be included in the permeate line 145 to pretreat the water before it reaches the water treatment module 110 as required by the particular application.

The water supply 120 provides a feed water stream having an original concentration of contaminants. The supply 120 may be, for example, a municipal water supply, a well, or any other source of water that is being treated.

The water treatment module 110 includes a feed water inlet 150 receiving the feed water stream from the feed water line 125, a waste water outlet 155 delivering the waste water stream to the waste water line 135, and a permeate outlet 160 delivering the permeate stream to the permeate line 145.

In the illustrated embodiment, the system 100 includes a prefilter 165 upstream of the water treatment module 110. The prefilter 165 may be integrated in the water treatment module 110 feed water inlet 155, in which case the water treatment module 110 may be characterized as multistage (e.g., a multistage RO module). The prefilter 165 may be provided in any form of filter that would benefit the performance of the contaminant sensor 175. Some examples of a suitable prefilter for different applications are a large contaminant filter, an organic material filter, a heavy metal filter, and a scale mitigation filter. The prefilter 165 removes large particulate contaminants, organic material, and/or heavy metals from the feed water by appropriate filtration means, such as polypropylene filters and active carbon filters. Organic contaminants could, for example, potentially foul sensors in the waste water line 135 as will be discussed below.

The system 100 also includes a contaminant detection system 170 that comprises a contaminant sensor 175, an optional pH reduction module 180, a water quality sensor module 185, and a processor 190. The contaminant detection system 170 may be a larger, permanently-installed system in the waste water line 135 or may be a handheld module taking a reading from a sample from the waste water line 135. Although illustrated schematically as separate components of the contaminant detection system 170, any two (or all three) of the contaminant sensor 175, pH reduction module 180, and water quality sensor module 185 can be provided in a combined module performing both (or all three) functions.

The term "contaminant sensor" is intended to be a very broad term, which includes electrical, electrochemical, optical, and fluorescent based sensors and any other sensor that senses a concentration of contaminants. Although the described embodiment refers to an electrochemical heavy metal sensor (and, at times, more specifically to a lead sensor), the invention is not limited to the described embodiment.

The contaminant sensor 175 may be, for example, an electrochemical sensor (which includes sensors classified as "electrical" sensors) for detection and measurement of contaminants in the waste water line 135. The contaminant sensor 175 may include microfabricated platinum electrodes that are able to detect the presence of lead as it builds up over time at the electrodes in the form of lead oxide. The microfabricated electrodes permit miniaturization of the contaminant sensor 175 which may be beneficial for handheld, portable applications. The rate of deposit of lead oxide is dependent on pH, temperature, conductivity, and ionic strength.

The contaminant sensor 175 may include a two-electrode system, a three-electrode system, or a four-electrode conductivity system, all of which are known in the industry. The two-electrode and four-electrode systems may include microelectrodes deposited on silicon dioxide substrates and the electrode material could be platinum, gold or other conductive metal. The three-electrode system includes a working electrode, a counter electrode (also called an auxiliary electrode), and a reference electrode. The electrodes may be microfabricated through deposition of various conducting materials or may be fabricated from carbon nanotube threads or from carbon nanotube fabrics or from graphene. The working electrode may include materials such as carbon, glassy carbon, carbon fiber, carbon nanothread, gold, platinum, bismuth oxide, boron doped diamond or other electrode materials known to the art. The counter electrode may include materials such as carbon, carbon nanothread, gold, platinum, or other electrode materials known to the art. The reference electrode may include materials such as carbon nanothread, silver/silver chloride, microfluidic or other electrode materials known to the art. A microfluidic reference electrode would provide superior stability and longevity compared to the other types of reference electrodes.

The function, including sensitivity, of the contaminant sensor 175 is closely tied to the function of the water treatment module 110. Known RO modules are typically capable of production of pure water at a rate of between 60-75%. Within such systems, the ionic concentration of various metal ions and oxides/hydroxides, including sodium, calcium, magnesium, potassium, and undesirable contaminants including lead, copper, and iron, can be as much as about 2-4 times as high in the waste water stream compared to the feed water. As the efficiency of RO modules improves, it is expected that the waste water stream will have concentrations that continue to rise. As RO modules increase in efficiency, the effective sensitivity of the contaminant sensor 175 of the present invention will also increase.

For example, a 90% efficient RO module would concentrate contaminants in the waste water stream by 10 times (one order of magnitude). The presence of 2 ppb of a contaminant in the feed water stream to a 90% efficient RO module would result in a contaminant concentration of 20 ppb in the waste water stream. If the contaminant were lead (Pb) in this example, the conductivity of the water would increase from about 200 μS/cm in the feed water stream to 2000 μS/cm in the waste water stream, which would significantly increase detection sensitivity and reduce measurement time of the contaminant sensor 175. Since the contaminant sensor 175 is positioned in the waste water stream, the detection sensitivity of the contaminant sensor 175 is effectively increased compared to positioning it the feed water stream. Additionally, the effectiveness of the contaminant sensor 175 is increased by inclusion of the prefilter 165 in the system 100 because organic compounds can reduce the effectiveness of the contaminant sensor 175.

It may be desirable to reduce the pH (i.e., increase the acidity) the of the waste water before introducing it to the contaminant sensor. For this purpose the pH reduction module 180 is provided upstream of the contaminant sensor 175. The pH reduction module 180 can alternatively be combined with the contaminant sensor 175 and/or the water quality sensor module 185 provided the pH reduction module 180 lowers pH prior to the other sensors taking readings. The pH reduction module 180 employs an electrochemical method, using two electrodes placed across a reverse osmosis or other semi-permeable membrane. The fluid at the cathode will experience a pH reduction (become more acidic), while the fluid at the anode will experience an increase in pH (become more basic). At lower pH (typically near 4.5), metal oxides present in water will convert to their ionic form. The ionic form of these metals is necessary for electrochemical detection at the contaminant sensor 175. At neutral pH, most of the metal oxides exist in a colloidal or particulate form. In this form, they are difficult to detect with known electrochemical contaminant sensors. However, an equilibrium condition is established between the solid (particulate) form and the ionic form that is a function of the solubility constant of the material as well as the surface area of the particulates. Particle size and water turbidity measurements may be used to estimate the quantity of lead or other metals that exist in the particulate form. In the event that the electrochemical contaminant sensor 175 is of a type that is able to detect and measure contaminants at neutral pH, the pH reduction module 180 can be eliminated from the contaminant detection system 170. An example of a potential contaminant sensor 175 operable at neutral pH is one based on carbon nanotube thread electrodes.

The contaminant sensor 175 may include instrumentation that allows for anodic stripping voltammetry, cyclic voltammetry or other electrochemical method for the detection of heavy metals in water or other fluid. The contaminant sensor 175 may include instrumentation that applies single frequency or multifrequency impedance spectroscopy techniques to evaluate the electrode condition to determine fouling of the electrode and solution conductivity. In one aspect of the invention, the electrodes of the contaminant sensor 175 (e.g., a three-electrode sensor having a working, counter, and reference electrode) and the water quality sensor module 185 (e.g., electrodes for pH, temperature, conductivity, ionic strength, and particle sensing) may all be connected via multiple channels to an instrument with functionalities such as potentiostat, impedance analyzer, and high impedance voltmeter. The contaminant sensor 175 may include instrumentation that monitors multiple channels for various water quality parameters, including pH, conductivity, temperature, among others, that can impact the detection of lead and other heavy metals by electrochemical methods.

The readings of the contaminant sensor 175 are affected by the water quality (which includes the water's chemistry and other factors) of the waste water stream, and the water quality should be understood to properly deduce the concentration of contaminants in the feed water stream based on the readings of the contaminant sensor 175. For example, as noted above, the rate of deposit of lead oxide on the contaminant sensor 175 is dependent on pH, temperature, conductivity, and ionic strength.

The water quality sensor module 185 is used to determine the water quality of the waste water stream. The water quality sensor module 185 may include multiple sensors for water quality factors such as pH, temperature, conductivity, ionic strength, particulate concentration, and impedance. For conductivity, for example, the water quality sensor module 185 may include an ionic sensor. The water quality sensor module 185 may include ion selective electrodes for sensing pH and ionic strength. The water quality sensor module 185 may be positioned upstream of the contaminant sensor 175 (as illustrated), downstream of the contaminant sensor 175, or integrated in a module containing both the water quality sensor module 185 and the contaminant sensor 175. As noted above, the water quality sensor module 185 may be combined with the pH reduction module 180 with or without also combining with the contaminant sensor 175. In one aspect of the invention, the water quality sensor module 185 may include microfabricated pH, temperature, ionic strength, conductivity and particle sensing electrodes on a single or multiple microdevice/microchip platform.

The water quality sensors in the water quality sensor module 185 enable the accurate quantification of contaminants in the waste water stream based on measurements of the contaminant sensor 175. For example, it is known that water having a relatively low (more acidic) pH will increase the concentration of heavy metals in their ionized form. Therefore, the readings of the contaminant sensor 175 can be adjusted to account for the pH level of the waste water. Also, the solubility of heavy metal compounds is affected by temperature and ionic strength. By sensing the temperature and conductivity of the waste water with sensors in the water quality sensor module 185, these factors can be considered when interpreting the readings of the contaminant sensor 175.

The water quality sensor module 185 may include integrated sensor that measures quantity and size distribution of metal particulates in the water via optical and impedance sensing modalities. The water quality sensor module 185 may include an integrated particle sensor to determine the size and quantity of contaminants. The integrated particle sensor determines size distribution of metal oxides that may be present and for calculations that provide information on rate of dissolution. The water quality sensor module 185 may include an integrated ion selective electrode pH sensor. The water quality sensor module 185 may include an integrated ion selective electrode metal ion sensor, including magnesium, calcium, sodium, potassium and ion selective electrode anion sensors, including chloride, for determination of ionic strength. The water quality sensor module 185 may include an integrated temperature sensor, based on microfabricated electrodes made of conducting metals, including gold and platinum. The water quality sensor module 185 may include an integrated conductivity sensor, based on microfabricated electrodes made of conducting materials such as gold, platinum and carbon. The water quality sensor module 185 may include a sensor that uses a combination of electrode materials for the specific detection of multiple heavy metals.

The processor 190 receives input from the water quality sensor module 185 and the contaminant sensor 175 to calculate the contaminant concentration in the waste water stream. The processor 190 is loaded with an algorithm that adjusts the concentration of contaminants (e.g., ionic and particulate lead) in the waste water stream based on pH, temperature, conductivity, ionic strength, particle size or any combination of these in the waste water stream. In one aspect of the invention, the algorithm uses information from the particle sensor to determine the size and quantity of lead oxide particles and consequently use this data along with electrochemical data to determine the total dissolved and particulate lead and other heavy metals.

When programmed with the characteristics (e.g., efficiency) of the water treatment module 110, the processor can deduce the contaminant concentration of the feed water stream and the permeate water stream. In this regard, the contaminant detection system 170 is capable of measuring contaminants (e.g., heavy metals) in water at the feed water inlet 150, waste water outlet 155 of a water treatment module, and permeate outlet 160 (e.g., a RO module). The The processor 190 may communicate with or include a user interface to permit the processor 190 to be programmed and/or to communicate contaminant concentration levels to an operator of the system 100.

As noted above, the contaminant detection system 170 can be integrated into the system 100 or may be provided as a handheld system. A handheld system may include a contaminant sensor 175 in the form of a sensor cartridge inserted into a portable, handheld contaminant analyzer. In addition to the contaminant sensor 175, the handheld system would include the processor 190 and one or both of the optional pH reduction module 180 and the water quality sensor module 185. Alternatively, one or both of the optional pH reduction module 180 and the water quality sensor module 185 can be provided separately from the handheld system.

The strategy of the present invention is different from known strategies in which chemical reagents or other additives (e.g., buffers that modify the pH, ionic environment, and conductivity) are combined with the water sample to condition the water to a predefined quality or chemistry profile before using a sensor to determine the contaminant concentrations in the sample. To the extent that pH of the waste water must be reduced to make the contaminant sensor 175 more effective, the electrochemical pH reduction module 180 described above can be used to reduce pH without additives. Additionally, by positioning the contaminant detection system 170 in the waste water stream where ions of contaminants are preconcentrated by the water treatment module 110, the effective sensitivity of the contaminant sensor 175 is increased.

In one aspect of the present invention, inclusion of an electrochemical cell and application of an electrochemical method for pH reduction of the inlet, outlet and waste stream water. pH adjustment for enhancing detection sensitivity will be achieved using two electrodes placed across a reverse osmosis or other semi-permeable membrane. The fluid at the cathode will experience a pH reduction (become more acidic), while the fluid at the anode will experience an increase in pH (become more basic). The low pH sample will facilitate the dissolution of any particulate metals/metal oxides into ions, which are needed for successful electrochemical detection.

One aspect of the invention provides a portable, hand held heavy metal analyzer comprising multiple water quality sensors including pH, conductivity, temperature and particle size distribution.

The system may include a heavy metal analyzer that possesses WiFi, Bluetooth or other wireless communication capabilities for transferring data to software on a device or in the Cloud. Devices may include cell phones, wireless routers, tablets, computers or other internet enabled device.

The disclosed invention provides a continuous, real time system for detection of contaminants without the need for chemical reagents or other additives. The system does not require calibration, despite changes to the electrode or environmental conditions.

Various features and advantages of the invention are set forth in the following claims.

The invention claimed is:

1. A water contaminant detection system, comprising:
a wastewater input in fluid communication with a waste outlet of a water treatment module, the water treatment module receiving a feed water stream;
a contaminant sensor configured to measure a concentration of a contaminant in a wastewater stream received from the waste outlet;
a water quality sensor module configured to measure a water quality parameter of the wastewater stream; and
a processor programmed to:
receive a measured concentration of the contaminant in the wastewater stream from the contaminant sensor;
receive a water quality parameter from the water quality sensor module;
obtain a predetermined efficiency value for the water treatment module; and
determine a concentration of the contaminant in the feed water stream based on the measured concentration of the contaminant in the wastewater stream, the water quality parameter, and the predetermined efficiency value.

2. The water contaminant detection system according to claim 1, wherein the contaminant sensor is configured to measure the concentration of contaminants selected from the group consisting of: dissolved solids, heavy metals, organic compounds, volatile organic compounds, biological contaminants, scale-forming contaminants, or a combination thereof.

3. The water contaminant detection system according to claim 1, wherein the contaminant sensor comprises at least one of an electrical sensor, an electrochemical heavy metal sensor, an optical sensor, and a fluorescent based sensor.

4. The water contaminant detection system according to claim 3, wherein the contaminant sensor consists of the electrochemical heavy metal sensor.

5. The water contaminant detection system according to claim 3, wherein the contaminant sensor is a three-electrode system including a working electrode, a counter electrode, and a reference electrode.

6. The water contaminant detection system according to claim 1, wherein the water quality sensor module comprises at least one of a pH sensor, a conductivity sensor, a temperature sensor, an ionic strength sensor, a particle size sensor, and a fluid turbidity sensor.

7. The water contaminant detection system according to claim 6, wherein the water quality sensor module consists of the conductivity sensor.

8. The water contaminant detection system according to claim 6, wherein the water quality sensor module includes two or more sensors provided on a single microchip platform.

9. The water contaminant detection system according to claim 1, wherein the contaminant detection system further comprises an electrochemical pH reduction module for lowering the pH of the wastewater stream prior to the wastewater stream reaching the contaminant sensor.

10. The water contaminant detection system according to claim 9, wherein the electrochemical pH reduction module includes a first electrode and a second electrode positioned across a semi-permeable membrane.

11. The water contaminant detection system according to claim 10, wherein the electrochemical pH reduction module is configured to reduce the pH of the wastewater stream to an acidic pH.

12. The water contaminant detection system according to claim 1, wherein the contaminant detection system comprises a handheld device.

13. The water contaminant detection system according to claim 1, wherein the contaminant is lead.

14. The water contaminant detection system according to claim 1, wherein the processor is further programmed to provide the concentration of the contaminant in the feed water stream to a user interface.

15. A method for determining contaminant concentration in a feed water stream, the method comprising:
   receiving a wastewater stream from a waste outlet of a water treatment module, the water treatment module receiving the feed water stream;
   measuring a concentration of the contaminant in the wastewater stream;
   measuring a water quality parameter of the wastewater stream;
   obtaining a known efficiency value for the water treatment module; and
   using a processing unit, determining a concentration of the contaminant in the feed water stream using the water quality parameter, the concentration of the contaminant in the wastewater stream, and the known efficiency value.

16. The method according to claim 15, wherein the contaminant is one of: dissolved solids, heavy metals, organic compounds, volatile organic compounds, biological contaminants, and scale-forming contaminants.

17. The method according to claim 16, further comprising electrochemically reducing a pH of the wastewater stream prior to measuring the concentration of the contaminant.

18. The method according to claim 15, wherein the contaminant is lead.

19. The method according to claim 15, further comprising providing the concentration of the contaminant in the feed water stream to a user interface.

20. A water contaminant detection system, comprising:
   a wastewater input in fluid communication with a waste outlet of a water treatment module, the water treatment module receiving a feed water stream;
   a pH reduction module for lowering the pH of a wastewater stream received from the waste outlet, the pH reduction module generating a reduced pH wastewater stream;
   a contaminant sensor configured to measure a concentration of a contaminant in the reduced pH wastewater stream;
   a water quality sensor module configured to measure a water quality parameter of the reduced pH wastewater stream; and
   a processor programmed to:
      receive a measured concentration of the contaminant in the reduced pH wastewater stream from the contaminant sensor;
      receive a water quality parameter from the water quality sensor module;
      obtain a predetermined efficiency value for the water treatment module; and
      determine a concentration of the contaminant in the feed water stream based on the measured concentration of the contaminant in the reduced pH wastewater stream, the water quality parameter, and the predetermined efficiency value.

* * * * *